United States Patent [19]

Flood et al.

[11] 4,105,122
[45] Aug. 8, 1978

[54] INSPECTING CANS FOR OPENINGS WITH LIGHT

[75] Inventors: John Michael Flood; Clifford Harry Messervey, both of Randolph, N.Y.; Richard Dye, Bloomfield, N.J.; Leo Patrick O'Connor, Jamestown, N.Y.

[73] Assignee: Borden, Inc., Columbus, Ohio

[21] Appl. No.: 745,191

[22] Filed: Nov. 26, 1976

[51] Int. Cl.² .......................................... B07C 5/344
[52] U.S. Cl. ..................................... 209/73; 209/75; 209/111.7
[58] Field of Search ................... 209/73, 74, 111.7 R, 209/111.6, 75; 356/237; 250/223 R

[56] References Cited

U.S. PATENT DOCUMENTS

| | | | |
|---|---|---|---|
| 3,416,659 | 12/1968 | Linderman et al. | 209/111.7 |
| 3,750,877 | 8/1973 | Cvacho | 209/73 |
| 3,826,923 | 7/1974 | Trimble | 250/223 R |
| 3,991,882 | 11/1976 | Fahnestock | 209/73 |

Primary Examiner—Allen N. Knowles
Attorney, Agent, or Firm—George A. Kap; George P. Maskas; Daniel D. Mast

[57] ABSTRACT

Inspection is effected by clamping cans between a holder and a photosensitive device which holders and devices are disposed in opposed relationship in a plurality of sets, illuminating exterior of the cans to project light through any opening in the can to the photosensitive device, sensing such light and sending electrical signals to an electronic memory to sort good cans from leakers; the photosensitive device includes an array of directional photodarlingtons one group of which detects openings in can flanges and another group detects openings in can bodies.

40 Claims, 17 Drawing Figures

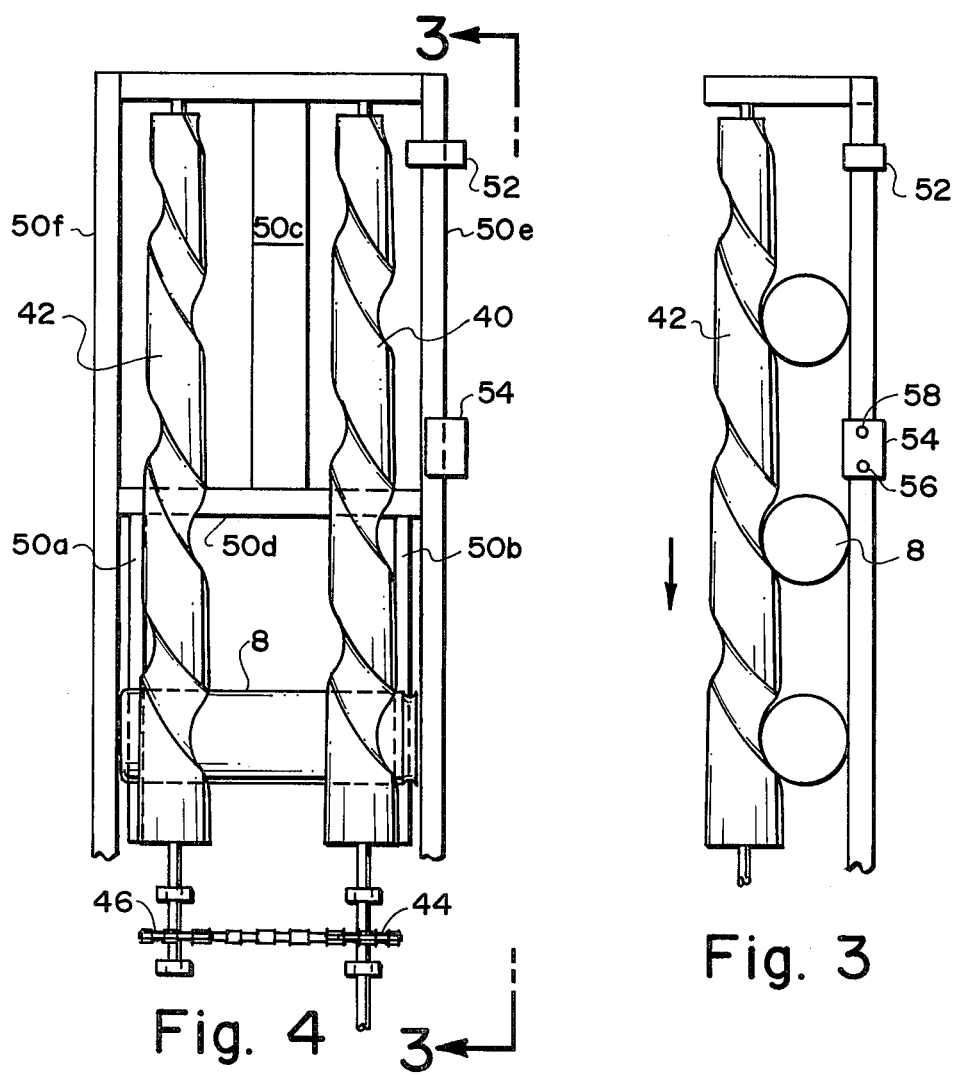
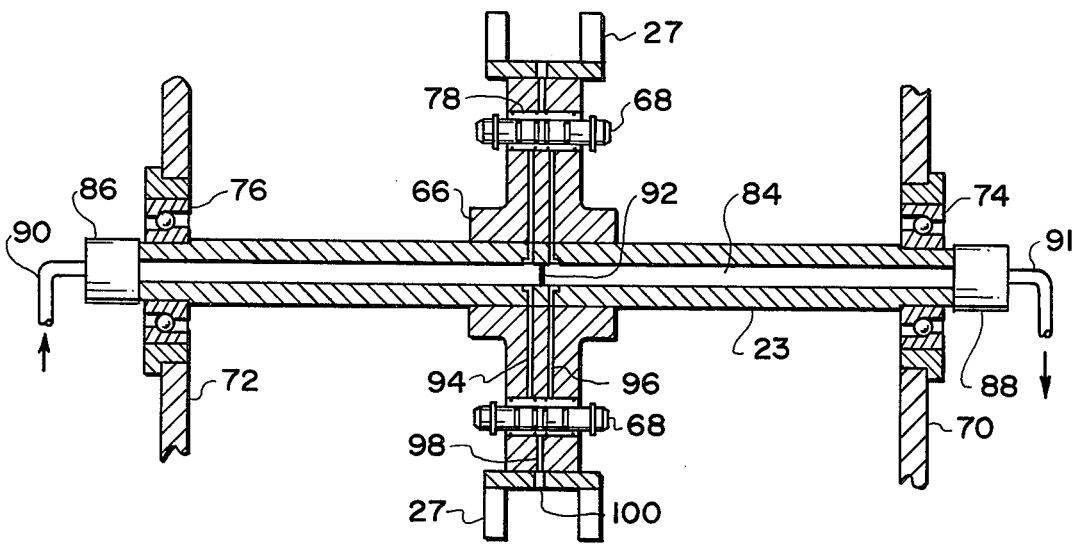

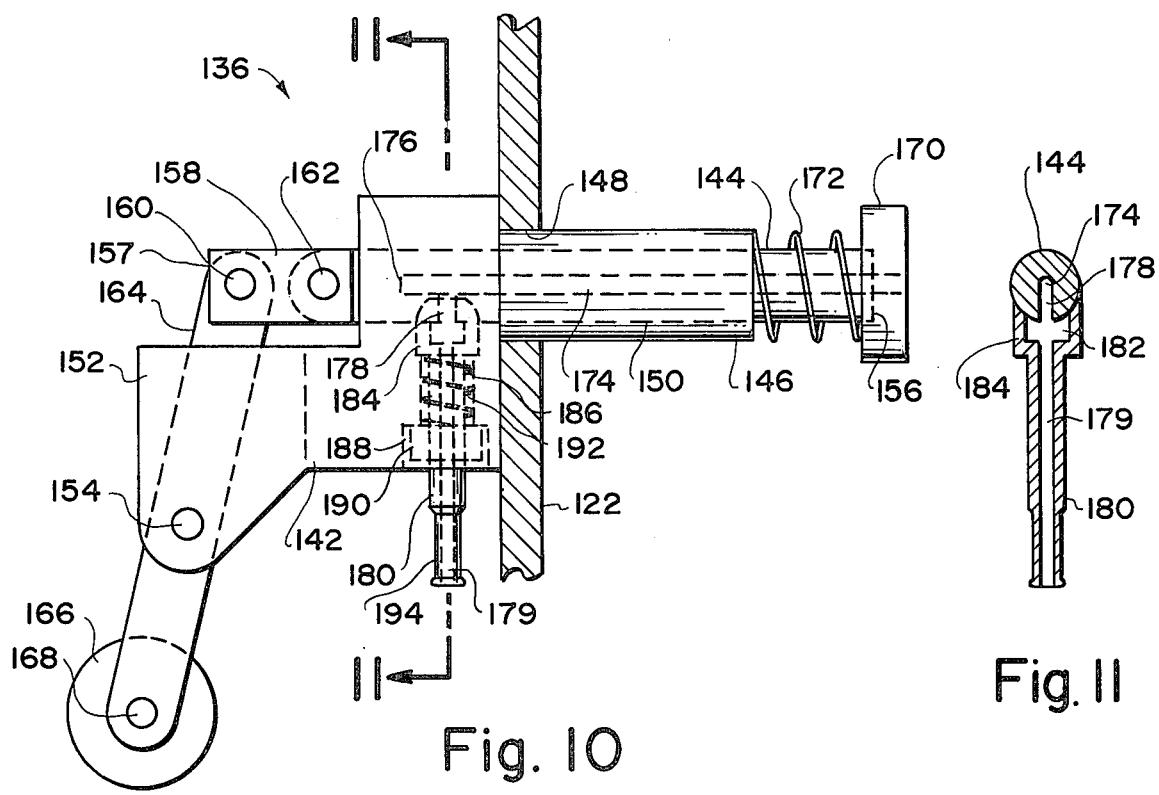
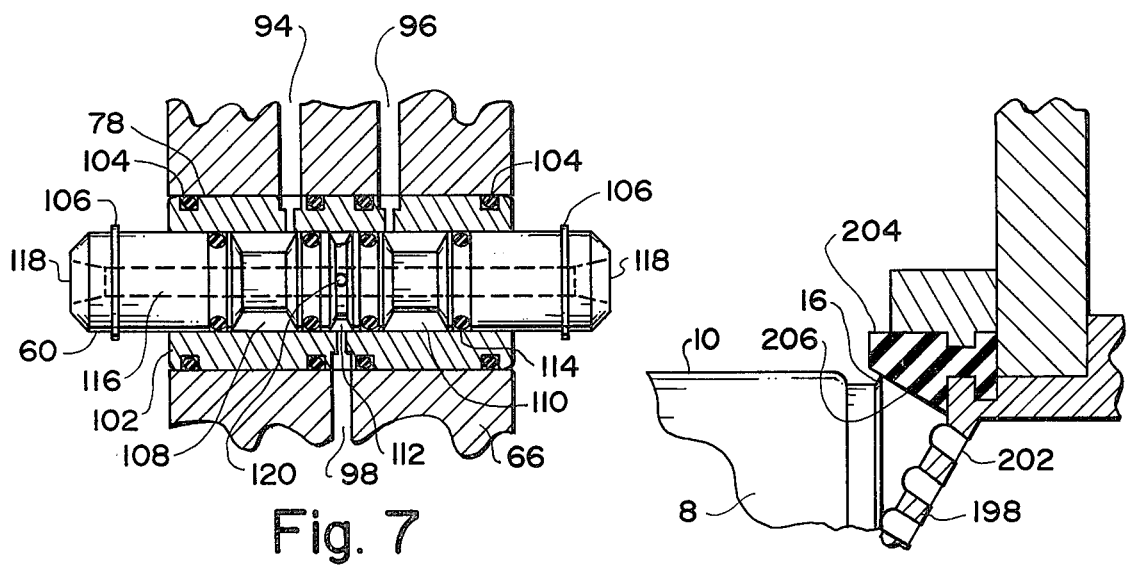

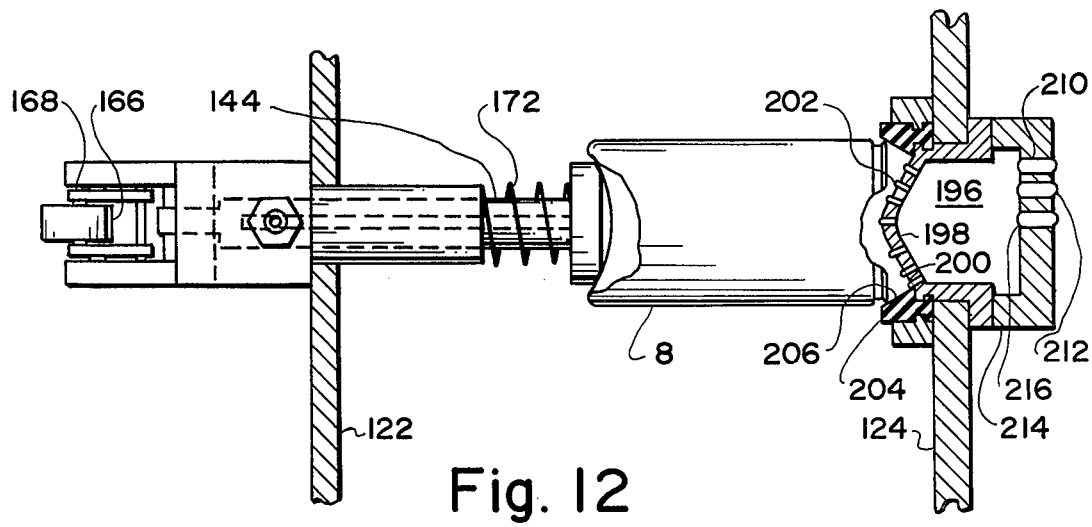
Fig. 12
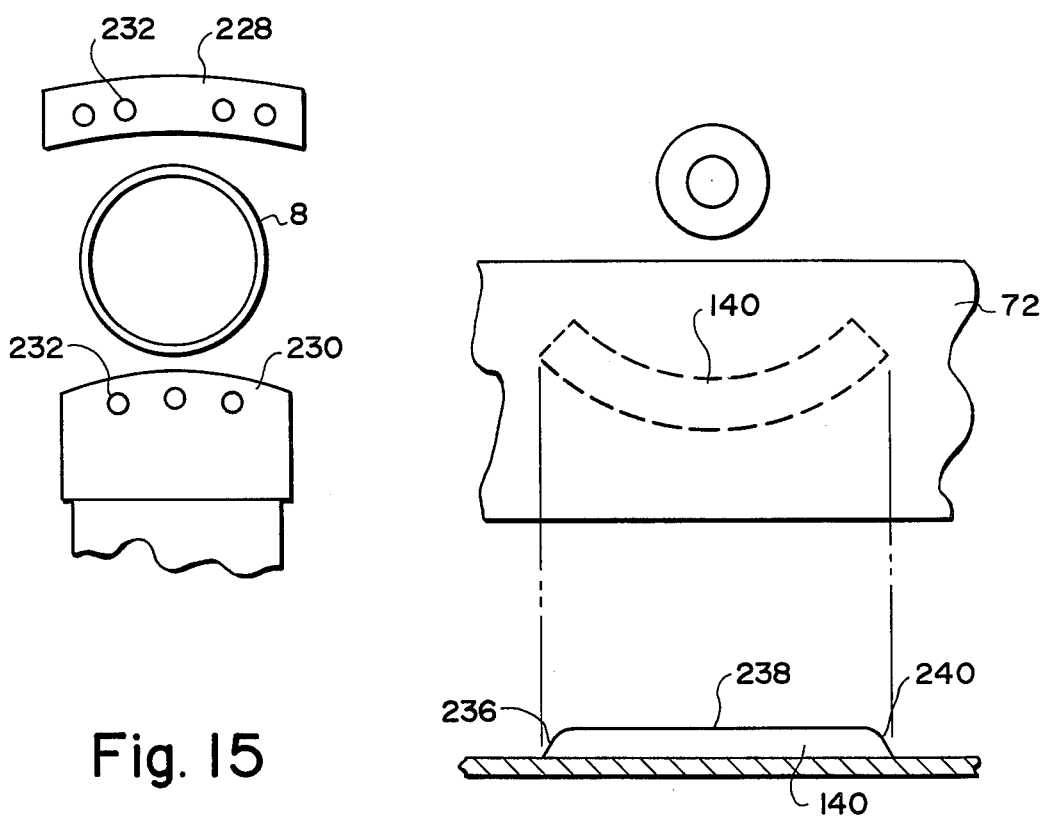
Fig. 15
Fig. 16

INSPECTING CANS FOR OPENINGS WITH LIGHT

The use of pressurized air for testing can bodies for presence of openings therein has been a common practice for many years. Illustrative of such air testers is the Borden tester disclosed in the Messervey et al U.S. Pat. No. 3,750,348 (73/45.1). More recently, testing of can bodies has been revolutionized by the advent of light testers where visible light is used as a medium for detecting openings in can bodies. The Cvacho et al U.S. Pat. No. 3,750,877 (209/73), assigned to Reynolds Metals Company, is illustrative of the light testers. The shift from air testers to light testers is due mainly to a lower total cost of the light testers versus air testers and an enormously lower maintenance cost of light testers compared to air testers. The cost of pumping air, in the case of air testers, is expensive as well as maintenance of rubber pads, air cylinders and many more structural elements. The air tester is a much bulkier and a larger piece of equipment than the light tester, consequently requiring much more space. In terms of structural and mechanical complexity of the two types of testers, the light testers are relatively uncomplicated.

In addition to the two patents mentioned above, of which the Reynolds U.S. Pat. No. 3,750,877 is believed to be most pertinent since it uses light as the testing medium in connection with testing of can bodies, the following is prior art known to applicants which is believed to be especially pertinent.

| | |
|---|---|
| 2,318,856 (209/82) | 3,351,198 (209/111.6) |
| 2,332,308 (201/111) | 3,415,370 (209/111.7) |
| 2,453,720 (209/111) | 3,416,659 (209/111.7) |
| 2,682,802 (88/14) | 3,453,054 (356/237) |
| 2,872,039 (209/111) | 3,499,314 (73/45.2) |
| 2,886,716 (250/219) | 3,724,655 (209/73) |
| 3,218,463 (250/222) | 722,967 (German) |

The light tester claimed herein is adapted for detecting openings in containers by means of light. It comprises a rotatable shaft; plurality of photosensitive devices mounted for rotation with the shaft; plurality of holders, corresponding in number to the number of the photosensitive devices, mounted for rotation with the shaft with each holder disposed opposite a corresponding photosensitive device, the holder includes means for maintaining the container between the holder and the photosensitive device whereby the device shuts-off the open end from exterior light; means for feeding the containers between cooperating holders and the photosensitive devices; stationary test station, including a light source for illuminating exterior of the containers passing therethrough with the photosensitive devices sensing light passing through any opening that may be present in the container; and means for sorting good containers from leakers in response to signals from the photosensitive devices.

A preferred embodiment of the subject light tester is illustrated in the appended drawings wherein:

FIG. 3 is a side view of the screw conveyor feed with cans disposed between screw flights, proximity switch to test presence of cans and a cookie cutter tester or flange detector for determining presence of flanges;

FIG. 4 is a rear view of the feed screw conveyor which shows nestling of cans between screw flights and side-by-side arrangement of the pair of screws;

FIG. 6 is a cross-sectional view of the feed wheel and its associated structure including front and rear plates and a shaft disposed therebetween for mounting the feed wheel;

FIG. 7 is an enlarged view of the lower spool shown in FIG. 6, mounted on a disc;

FIG. 10 is a side view of one of the holders which projects through a ring to clamp a can against a cooperating photosensitive device;

FIG. 11 is a partial cross-sectional view of FIG. 10 taken along plane 11—11;

FIG. 12 shows the holder in its operative extended condition clamping a can against a cooperating photosensitive device and details of the photosensitive device;

FIG. 13 is an enlarged view of a portion of FIG. 12 illustrating the relationship of the can flange and the conical surface of the photosensitive device, which arrangement allows detection of openings in the can flanges;

FIG. 15 shows a simplified version of the upper and lower light fixtures with a can disposed therebetween;

FIG. 16 is a view of front plate and disposition of the cam track on its opposite side, with the track being also defined in a horizontal view.

To facilitate understanding, the apparatus is initially described by reference to a schematic illustration of it in FIG. 2 in order to provide a conceptual understanding thereof and relative arrangement of its principal components. This is followed by detailed explanation of the apparatus and its parts in connection with additional figures thereof.

Figure 1:
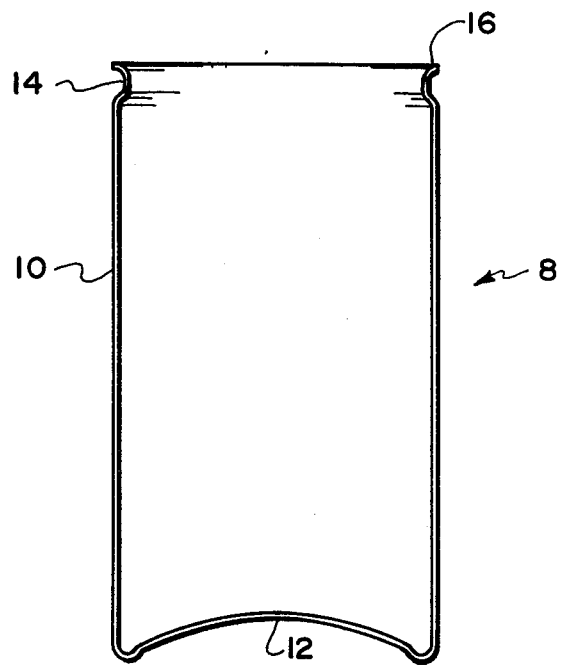
FIG. 1 is a cross-sectional view of a drawn metal can which includes a bottom, body, neck, and flange.

This apparatus is adapted for testing containers for the presence of openings therein. The openings can be in the form of pinholes, larger holes, slits, cracks, and in general, any discontinuity in the structure of the container which admits light thereinto causing damage to the contents of the container by leakage or admission of air which contributes to spoilage of its contents. Any container, open at one or both ends, made of plastic, metal such as steel or aluminum, or any other material, can be tested on this apparatus where the material is such that the opening is relatively well defined to allow light penetration. As used herein, the term "open-ended container" shall mean a container with one or both ends open. Especially preferred for testing in our apparatus are metal cans known as drawn cans, one of which is illustrated in FIG. 1, where can 8 is shown with body 10, integrally formed bottom 12, neck 14 and flange 16. In a drawn can, bottom 12 is substantially of the same thickness as the original disk stock which is inspected for openings before it is formed into a can. For this reason, it is not necessary to test the bottom of a drawn can for presence of openings. The rest of the can, i.e., body, neck and flange, are ironed or drawn in the forming process to a fraction of its original thickness during which operation, openings may be formed.

In its preferred embodiment, this apparatus rejects cans by sensing direct rays of light from an outside light source and not by light reflected from inside wall thereof before it enters a photosensitive device. The photosensitive devices used in the preferred embodiment are sensitive to a degree that reflected light will not energize same because it loses too much of its intensity on reflection. If the opening is of a very large size, not normally encountered in cans, and allows penetration of light of very high intensity, then in such an instance, it is likely that the reflected light may have sufficient intensity to activate a photosensitive device, however, the size of openings in cans is normally such that only direct light will energize the photosensitive device.

The principle of direct light activation of a photosensitive device has been demonstrated on a drawn can, such as shown in FIG. 1, which had a pinhole opening approximately 0.005 inch in size in its body. The open end of the can was closed with our photosensitive device and a lamp of 150 watts was moved around the can at a distance of about a quarter of a foot to apply light to the exterior of the can. It was observed that the opening was detected only when the lamp was in a specific position with respect to the opening to convey light rays directly into the photosensitive device, otherwise, the photosensitive device was not activated.

Sensitivity of this apparatus is such that it can detect openings at least as small as 0.001 inch when direct light passes therethrough to the photosensitive device. The inspection medium is radiant energy in the form of light which is visible to the eye although the ultimate criterion is any radiant energy which can be detected by a photosensitive device. In a preferred embodiment, high intensity quartz-iodine lamps are used to illuminate the exterior surface of the cans. These lamps have a high output of infrared light which is not readily reflected from most surfaces and for this reason, location of the opening can be easily ascertained by using directional photodarlingtons since essentially direct light is detected thereby. Particulars of the photosensitive device will be described later.

Figure 2:
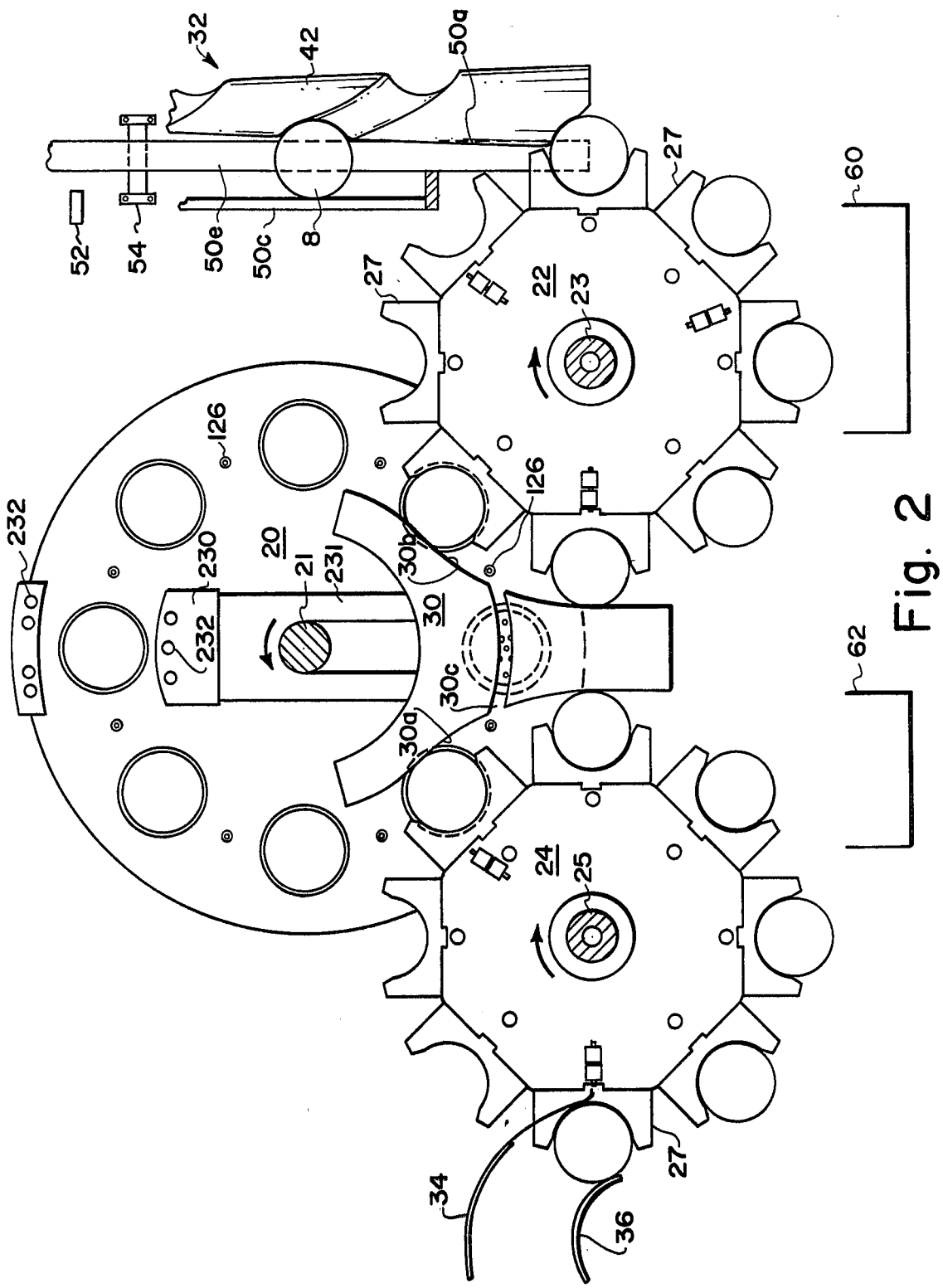
FIG. 2 is a simplified schematic view of the light tester showing relative disposition of the screw conveyor feed, feed wheel, test wheel and discharge wheel, and some of the associated structural elements.
Figure 9:
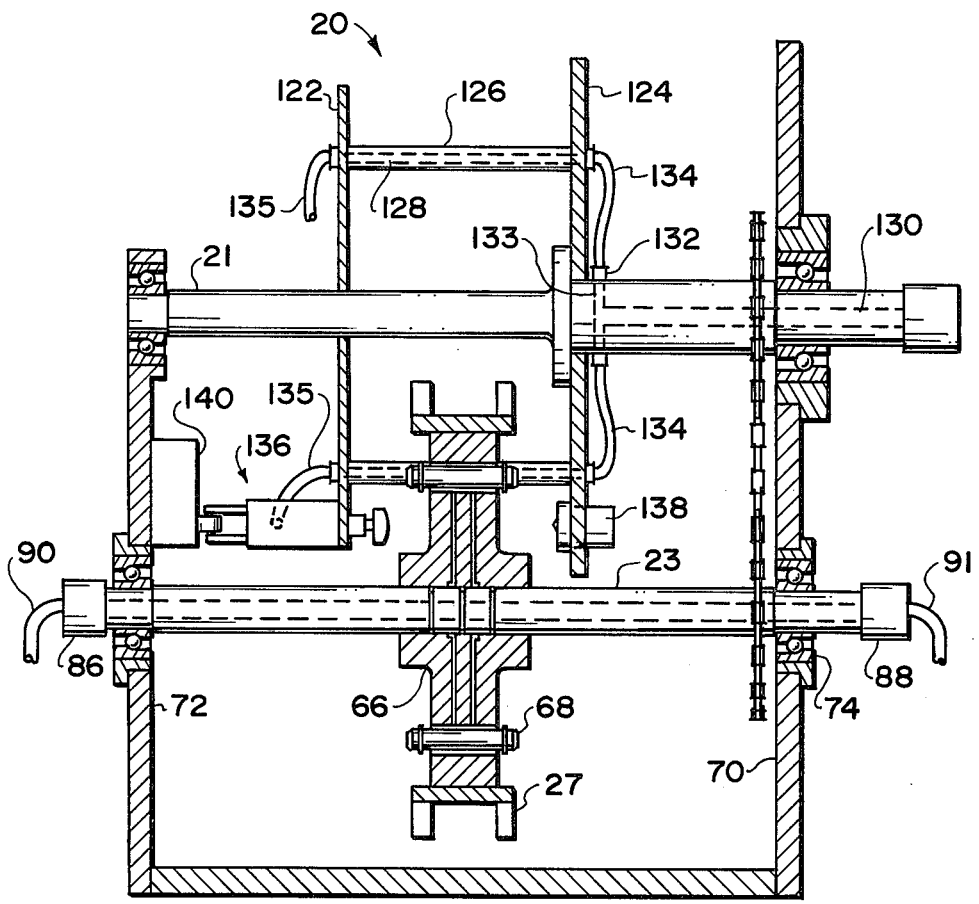
FIG. 9 is a cross-sectional view of the light tester illustrating disposition of front and rear plates, feed wheel, and test wheel as defined by a pair of spaced rings one having a plurality of holders mounted thereon circumferentially and the other having the same number of photosensitive devices disposed in opposing relationship to the holders.

FIG. 2 is a schematic illustration of the general disposition of test wheel or test carrier 20 mounted on shaft 21, rotatable counter-clockwise, in association with feed wheel or feed carrier 22 mounted on shaft 23, rotatable clockwise, and discharge wheel or discharge carrier 24 mounted on shaft 25, also rotatable clockwise. Test wheel 20 and the feed and discharge wheels 22, 24 are disposed in the same vertical plane and the respective shafts are journalled in a pair of spaced, vertically disposed side plates with the wheels residing therebetween, as will be described in more detail later. Each feed and discharge wheel is provided with cradles 27 which can eject a can by means of air pressure or retain a can therein by means of vacuum, as will be described. Double guide rail 30, which is stationary, is disposed below shaft 21 on the test wheel and has a pair of flared surfaces 30a, 30b which cooperate with cans in either loading or unloading thereof into or out of test wheel 20. Slot 30c devides the double guide rail 30 into an upper section and the lower section. The upper section is secured to bracket 231 whereas the lower section is secured between front and rear plates 72, 70, see FIG. 9. The purpose of slot 30c is to provide clearance for brace rods 126 which space rotatable rings 122, 124, which are shown in FIG. 9. Feed conveyor 32 is synchronized with rotation of feed wheel 22 to deliver cans into cradles 27 in timed sequence, which cans are held in the cradles by means of vacuum, whereas rails 34 and 36 are associated with discharge wheel 24 in facilitating the handling and transfer of cans from the discharge wheel. The cans are loaded into the feed wheel 22 by means of screw conveyor 32, transferred from the feed wheel to test wheel 20 where they are tested, transferred from test wheel to discharge wheel 24 and then to one of two hoppers, depending whether a can is good or leaky.

As shown in more detail in FIGS. 3 and 4, screw conveyor 32 moves cans in the direction of the arrow shown in FIG. 3 by means of a pair of screws 40, 42 which are mounted in bearings and driven in unison by chain driven sprockets 44, 46. These sprockets are indirectly driven by the same eddy current motor which drives the feed, test and discharge wheels with means provided for varying the speed of the screw conveyor. Cans 8 are disposed between screw flights and are moved by the rotation of the screw conveyor. Confining rails 50a, 50b serve to maintain the cans between the screw flights in horizontal disposition which function is performed by central rail 50c at the upper extremity of the conveyor. Transverse rail 50d is mounted between longitudinal flange rail 50c and can bottom rail 50f. Proximity switch 52 and flange detector 54 are mounted on flange rail 50e which is disposed adjacent can flanges as the cans are moved into the feed wheel. The can bottom flange is mounted on the other side of the moving cans. Both flange and can bottom rails guide the cans in their horizontal disposition to the feed wheel.

Shown in FIG. 3 is proximity switch 52, which senses presence of cans, and a cookie cutter detector 54, which tests cans for presence of flanges 16. Whenever presence of a can is sensed by the proximity switch, it energizes the cookie cutter detector which projects light from light source 56 onto the can flange 16 and the reflected light from the can flange is sensed by photocell 58. The light source and the photocell are disposed in such a way that light emitted by the light source is reflected by flange 16 into the photocell. If a can does not have a flange or the flange is damaged, no light is reflected from the light source into the photocell, which fact is conveyed by a signal to the memory which signals to energize a bumper roll in order to eject the can.

In the preferred embodiment, the tester herein utilizes a pair of cookie cutter detectors, as shown in FIG. 2, although it should be understood that one such detector can be used effectively. A pair of such detectors arranged in opposing relationship provides superior performance with fewer false rejects.

As cans move downwardly in screw conveyor 32, they are deposited by the conveyor into cradles 27 of feed wheel 22 at about the 1:30 o'clock position on the feed wheel. Beyond this point and until about the 6:00 o'clock position, vacuum holds the cans in the cradles. If a can is unflanged, the electronic memory will actuate and eject the unflanged can by means of air pressure at about the 6 o'clock position and this reject will wind up in hopper 60, see FIG. 2. If a can has a proper flange, it will be held in cradle 27 by means of vacuum until it is transferred to test wheel 20, which takes place at a point of about 10:30 o'clock position on the feed wheel. Function of the test wheel is to determine if a can is good or a leaker, and if it is the latter, memory shall receive a signal and expel the can at an appropriate time, otherwise the can is deposited with other good cans at another station.

After a can has been moved into the test wheel and the testing operation has been completed, the can is then transferred from the test wheel to the discharge wheel. If the can is a leaker, memory will actuate a mechanism and the can will be discharged from the discharge wheel by air pressure into hopper 62, see FIG. 2, and if the can is good, it will be retained by means of vacuum in the cradle until it reaches a position of about 9 o'clock when the can is stripped by stripper rail 34 onto rail 36.

Figure 5:
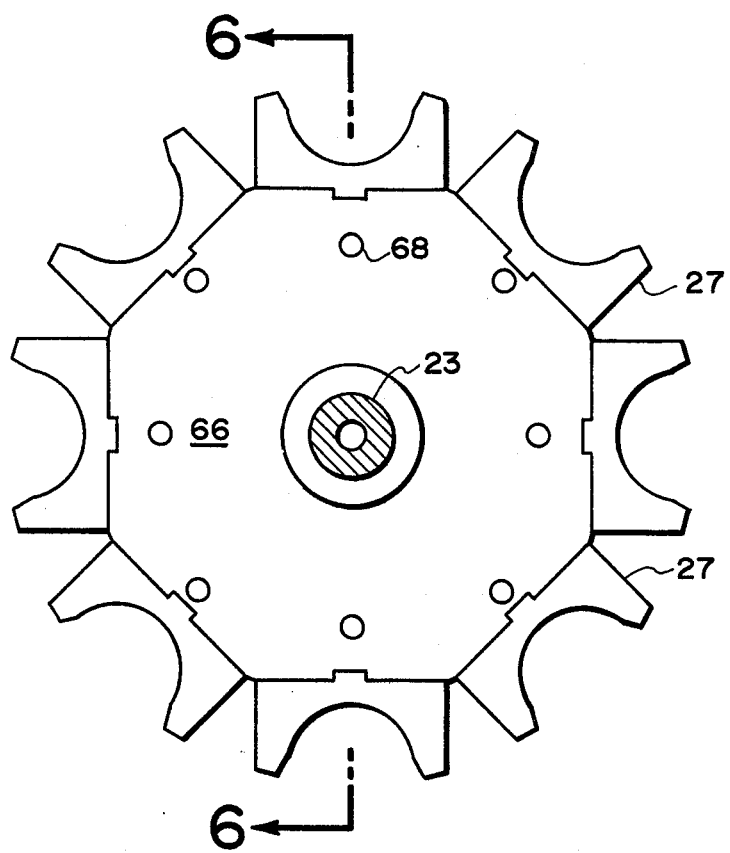
FIG. 5 is a front view of the feed wheel, which is identical to the discharge wheel except for a couple of minor differences, showing the central disk, can cradles mounted on the periphery of the disc and a spool valve in association with each cradle arranged in two concentric circles.

FIG. 5 illustrates a feed wheel which is identical in structure to the discharge wheel, with a number of minor differences. It includes a disc 66 having a plurality of cradles 27 bolted thereto. Spool valves 68 are provided in connection with each cradle with alternate spools mounted on a pair of concentric circles of different diameters. In the preferred embodiment, there are eight cradles arranged on a pair of concentric circles. Although eight spools and cradles are shown, it should be understood that this number may vary to accommodate any design requirement. The alternate setting of the spools on different concentric circles gives more time for each spool to be operated and for vacuum or pressure to be established.

FIG. 6, which is a partial cross-sectional view of FIG. 5, shows more details of construction of the feed wheel. Shaft 23 is mounted for rotation in rear plate 70 and front plate 72 by means of bearings 74, 76. Rigidly mounted on the shaft is disk 66 of feed wheel 22 with cradles 27 and spools 68 disposed in bores 78 passing through disk 66. Bumper rolls move spools from neutral to pressure position and back to neutral or from neutral to vacuum and back to neutral position.

Shaft 23 is hollow from end to end having a concentric port 84 communicating with a rotary unit 86 at one end and another rotary unit 88, at the other. Rotary unit 86 is connected to line 90 carrying pressurized air at about 35 psi whereas the other unit is connected to a vacuum line 91 which can provide vacuum of 20 inches of water, in the preferred embodiment. Air-tight divider 92 separates port 84 into two compartments: one of which is under pressure whereas the other is under vacuum.

Each spool 68 communicates with both compartments of port 84 by means of port 94, which connects to the pressure compartment, and port 96, which connects to the vacuum compartment. Another port 98 connects the spool with orifice 100 in cradle 27.

FIG. 7 is an enlargement of the bottom spool shown in FIG. 6, and its associated structure. Bushing 102 is disposed in bore 78 of disk 66. A plurality of O-rings 104 hermetically seal bushing 102 in bore 78. Spool 68 is slidably disposed in bushing 102 with snap-rings 106 limiting axial travel thereof. A pair of wide ports 108, 110 are provided on the spool symetrically with respect to the vertical axis of the spool and a narrow port 112 is disposed on the vertical axis itself. The ports are circumferential depressions in the cylindrical spools which are sealed from each other by O-rings 114. A longitudinal passage 116 through the horizontal axis of the spool is closed off at both ends by plugs 118. An opening 120 in the spool provides communication between port 112 and passage 116 for the purpose to be described.

The arrangement of the ports is such that when a spool is shifted to the right, port 94 allows pressurized air into port 108 and then into port 98 and through orifice 100 to expel a can from cradle 27. When spool is shifted to the left, port 96 draws vacuum on ports 110 and 98 allowing vacuum to retain a can in the cradle. Bumper rolls are arranged in such a manner that shifting is made from neutral to either side and back to neutral, and not from vacuum to pressure, or vice versa. In the neutral position of the spool, port 98 is disposed directly in alignment with port 112 which is closed-off by bushing 102.

Port 112 and opening 120 play an important role in facilitating testing of cans at a very high rate of 1200 cans per minute and higher. When the spool is shifted to the left in order to draw vacuum on port 98 so that a can in the cradle can be retained, port 96 is in communication with port 98 through port 110. In this position, port 94 is disposed over port 112 and admits pressurized air into passage 116 through opening 120. Since there is no outlet for the air, passage 116 acts as a reservoir of pressurized air. On shifting the spool to the right, port 112 is disposed over port 98 which previously had been under vacuum holding a can in the cradle. When communication is established between ports 112 and 98, pressurized air in passage 116 rushes into port 98 and instantaneously breaks the vacuum therein thus allowing the can to be discharged without any delayed holdover. As already explained, this allows rapid operation of the tester since the vacuum grasp on the cans in the cradles is quickly neutralized by the burst of pressurized air from passage 116. The effect of vacuum in passage 116 on pressurized condition is negligible when the spool is shifted from the right position to neutral.

Figure 8:
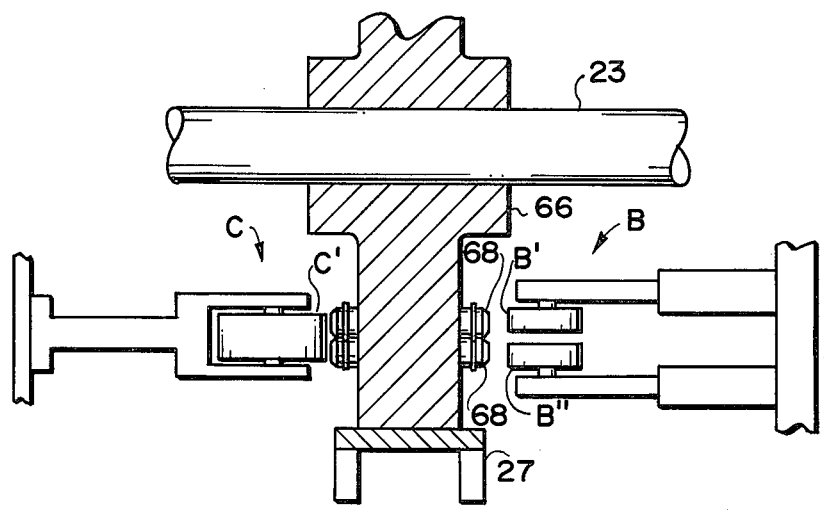
FIG. 8 shows a general disposition of the bumper rolls with respect to the spool valves mounted in the feed wheel.

Spools are displaced by means of bumper rolls, such as B and C shown in FIG. 8. The bumper rolls are mounted on brackets secured to the front and rear plates 72, 70. Since there are two concentric rows of spools, some bumper rolls we use are of double variety shown in FIG. 8 where roller B' actuates one row of spools and roller B" actuates the other row. It should be apparent that the use of double bumper rolls is economical in that a single bracket can be used to mount both bumper rolls. Single bumper roll is used when it is desired to return all of the spools to a predetermined position. Example of this is roll C' in FIG. 8.

As already described, cans without flanges or with damaged flanges are discharged from the feed wheel with air pressure into hopper 60 and good cans are conveyed clockwise and transferred from the feed wheel into the test wheel 20. As shown in FIG. 9, test wheel 20 includes holder ring 122, on which holding devices are mounted, and ring 124, on which the photosensitive devices are disposed. Rings 122, 124 are interconnected by hollow brace rods 126 which have passages 128 extending from end to end. The brace rods maintain rings 122, 124 in spaced relationship rotating on main shaft 21 which, in turn, is provided with a dead end bore 130. Nipples 132 on main shaft 21 communicate with bore 130 at the front end thereof through openings 133 arranged radially in the main shaft and corresponding in number to the number of brace rods 126. Nipples 132 are connected to tubing 134 and convey vacuum to holders 136 via brace rods 126 and tubing 135. Holders 136 are disposed on the same horizontal axis as the photosensitive devices 138 affixed to ring 124. A can is moved by the feed wheel into position between holder 136 and photosensitive device 138 nestled against guide rail 30b until its horizontal axis is in alignment with the horizontal axis of the holder and the photosensitive device, at which moment, the holder is actuated to force the can against the photosensitive device. The can is maintained in this position until it is transferred from the test wheel to the discharge wheel. The holder is in its operable or extended position and is rendered inoperable or is retracted when a roller secured thereto encounters and is elevated by a cam track which disengages the holder from a can for a duration of about 90°.

FIGS. 10 and 11 illustrate can holder 136 in detail, which includes holder block 142, holder stem 144 and barrel 146. Barrel 146 is integral with holder block 142 and the two parts have a general outline of a pistol. Holder block 142 abuts ring 122 and is secured thereto by bolts whereas barrel 146 projects through hole 148 in ring 122. At the upper portion of holder 136, bore 150 passes through barrel 146 whereas at the lower extremity, block 142 is provided with a pair of prongs 152 and pin 154 passing through an opening in the prongs. Holder stem 144, which is preferably cylindrical, is slidably disposed in bore 150 of barrel 146 and projects beyond the barrel terminating at the front end 156 and at the opposite end 157. Rear end 157 of holder stem 144 is formed into flattened rectangular shank 158 with pins 160, 162 passing therethrough. Pin 162 is a butt pin which limits forward movement of holder stem 144. Link 164 is secured between prongs 152 by pin 154 and to holder stem 144 by pin 160. The lowermost portion of link 164 is attached to roller 166 by pin 168. Roller 166 is adapted to roll on a cam track for about 90° between about 4:30 and 7:30 o'clock positions during which interval, link 164 is pivoted about pin 154 to move holder stem to the left. During this 90°, the holder is inoperative whereas for remainder of about 270°, it is operative with the roller being off the cam track and with the can being in a clamped position between the holder and the photosensitive device, as illustrated in FIG. 12.

Front end 156 of holder stem 144 is provided with pad 170 which, in operative position, abuts a can bottom. Holder stem is spring-biased by means of spring 172 which maintains the stem in the thrust or forward position. Spring 172 is disposed between forward end of barrel 146 and the rear face of pad 170. The purpose of spring 172 is to yieldably clamp a can between pad 170 and photosensitive device 138, as shown in FIG. 12.

Holder stem 144 has a dead-end concentric bore 174 drilled from the forward end 156 to a point 176 near the opposite end. Passage 178 is drilled from exterior of holder stem 144 to the bore 174 and communicates with port 179 of valve 180. Chamber 182 at the tip of port 179 is enlarged relative to the size of passage 178 which facilitates making the connection between passage 178 and chamber 182. As shown in FIGS. 10 and 11, valve 180 has an enlarged saddle seat 184 which slidably straddles holder stem 144.

FIG. 10 illustrates valve 180 disposed in bore 186 which passes through holder block 142. Bore 186 is enlarged at its entrance to form bore 188 which is internally threaded and accommodates nut 190 having an external thread section. Valve 180 passes freely through an opening in nut 190 and is biased against holder stem 144 by spring 192 disposed around valve 180 between nut 190 and saddle seat 184. Nipple 194 of valve 180 is connected to tubing 135 which supplies vacuum medium from port 130 in main shaft 21 through hollow rods 126.

The vacuum is applied to the bottom of a can as the can rotates for about 270° in a clamped position between a holder and a photosensitive device in the test wheel. During this time, cam roller is disposed in the condition shown in FIG. 10 off the cam track, which will be described later, and passage 178 is in communication with chamber 182. Just before the can is to be transferred from the test wheel to the discharge wheel, cam roller 168 encounters the cam track with the result that link 164 is gradually pivoted to slowly withdraw holder stem 144 to release the can from its clamped disposition. As the holder stem 144 is slowly retracted to the left of FIG. 10, passage 178 remains in communication with chamber 182 for a moment longer because of the enlarged size of chamber 182. The continued momentary application of vacuum to the bottom of the can while stem 144 is being retracted, will also retract the can away from the photosensitive device thus allowing its transfer to the discharge wheel.

FIGS. 12 and 13 illustrate the photosensitive device 196 against which can 8 is clamped and which senses any light passing into the can from an outside source. The device includes convex support 198 with a plurality of small openings 200 of about 0.193 inch in diameter disposed on several concentric circles. A photosensitive element 202 is disposed in each opening 200 for sensing any light in the interior of a can. Each opening 200 is disposed at a right angle to support 198 for the purpose of positioning elements 202 so that they face certain portions of the can interior, as will be described later. Support 198 is held in cylindrical frame 204 having interior frustoconical surface 206 which is specifically designed to accommodate inspection of can flanges. As shown in FIG. 13, can flange 16 of can 8 abuts the frustoconical surface 206 leaving ample room for light to enter between the can flange and frame 204 and for photosensitive element 202 to detect any light passing through the flange.

As was already mentioned, the photosensitive elements 202 are disposed in the convex support 198 at right angles thereto so that they point to a specific portion of the can. This arrangement is necessitated by the fact that elements 202 have an angular response within which light is sensed. In our preferred embodiment, element 202 is functional through a total angular response of 20°, although it should be understood that others can be used as well. In this connection, it should be noted that an angular response is related to sensitivity of the element in that the wider the angular response, the less sensitive is the element. With this feature in mind, elements 202 in the outer circle are positioned so that they can receive and sense light passing through can flanges, as was described in connection with FIG. 13. All the elements in the outer circle are connected to flange light 210, which is lighted when one or more of these elements senses light passing through a can flange. The other elements are directed at can body 10 and are connected to body light 212. Flange light 210 and can body light 212 are light emitting diodes and are disposed in openings of cup 214 which is secured to the rear of photosensitive device 196.

Figure 14:
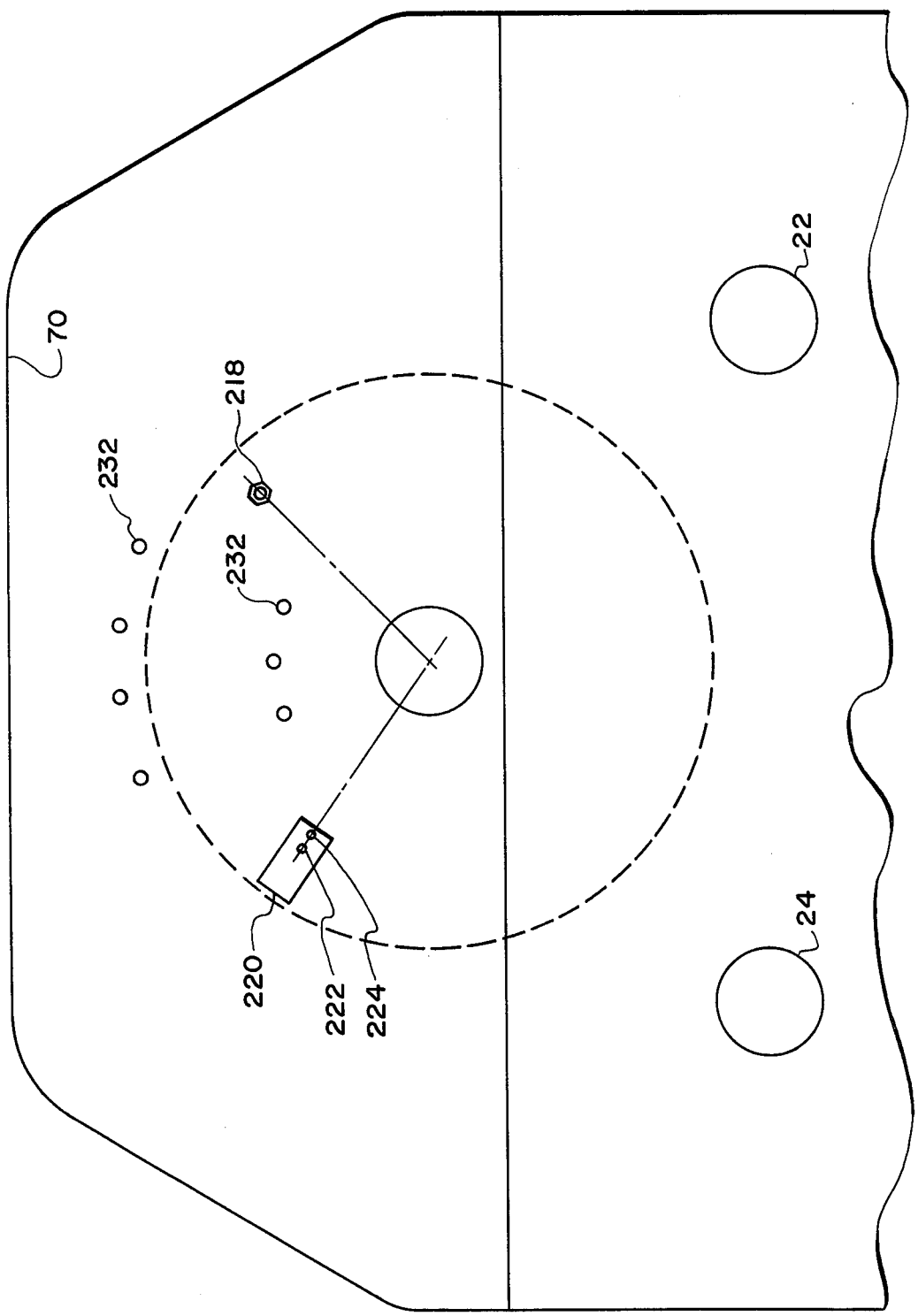
FIG. 14 is a frontal view of the rear plate showing a superimposed outline of the rear disk of the test wheel, the re-set device which re-sets body and flange lights at the beginning of a cycle and a photoreceiver for conveying signals from the flange and body lights to an electronic memory for separating good cans from leakers.

A phototransistor detector 216 also projects through the bottom of cup 214 and is actuated by a reset light 218, see FIG. 14, which is mounted on inner face of rear plate 70 at about the 1:30 o'clock position facing ring 124. Reset light 218 is necessary to extinguish the flange and body lights prior to the start of a new cycle, via phototransistor detector 216, which will have been energized on the previous cycle as the array was exposed to ambient light between discharge of previous can and clamping of present can. In this manner, the new cycle is commenced with the flange and body lights extinguished. Optical photoreceiver 220 is also mounted on the inner face of rear plate 70 at about 9:30 o'clock position facing ring 124. Photoreceiver 220 includes a pair of receiver sensors 222, 224 for detecting flange lights and body lights, respectively. Receiver sensors 222, 224 are connected to an electronic memory and convey signals for processing by the memory for ejection of cans at appropriate stations. Receiver sensors 222, 224 are also connected to a console which can be examined visually to determine condition of can flanges and can bodies.

Figure 17:
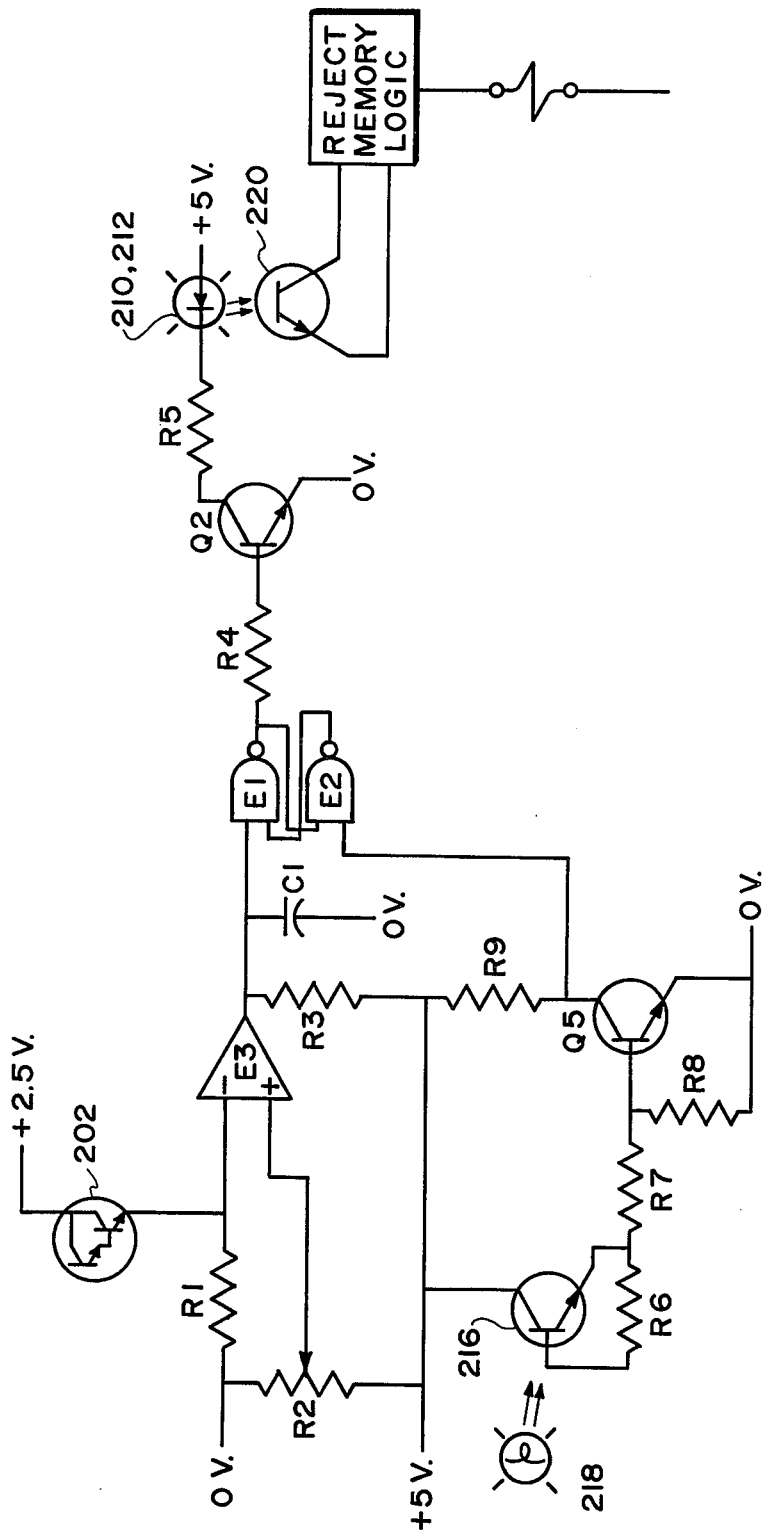
FIG. 17 represents simplified circuitry for processing light passing through an opening in a can by a photodarlington to reject the can at an appropriate station and for extinguishing flange and body lights which were energized by the photodarlington.

In order to facilitate understanding of how the flange and body lights are reset prior to commencement of the next cycle, reference is made to FIG. 17 which generally illustrates the relevant circuitry. Referring now to FIG. 17, irradiance of photodarlington 202, which is one of many comprising the photosensitive device 138, by external light passing through an opening in a can causes current to flow through photodarlington 202 and load resistor R1. Voltage drop across R1 is compared at the (−) input of amplifier E3 with the voltage present at (+) input of amplifier E3. This latter voltage, which is taken from potentiometer R2, is referred to as the set point. If the potential difference at (−) input of amplifier E3 exceeds that of (+) input, the output of amplifier E3 changes from +5 volts to an almost zero level. This change in voltage sets the flip-flop or temporary storage by Nands E1 and E2. The output of the flip-flop when set is +5 volts, which biases transistor Q2 into conduction. Current flowing through Q2 also flows through flange light 210 and/or body light 212, which are light emitting diodes, with R5 serving as a current limiting resistor.

The body and flange lights 210, 212 pass by stationary optical photoreceiver 220 which senses any irradiance of the body and flange lights and its output is amplified to a digital logic level for insertion into a reject memory. The memory actuates a mechanism for ejecting a defective can at a particular station. Resetting of the body and flange lights is accomplished by stationary reset light 218 which shines light on phototransistor detector 216. The output of detector 216 is used to switch transistor Q5 into conduction and the voltage at the collector of Q5 will go to essentially zero thus extinguishing the flange and body lights.

In FIG. 17, R4 is a bias resistor which controls voltage level to base of transistor Q2, as are R6, R7 and R8 which control voltage level to base of transistors Q3 and Q5. R3 is load resistor which limits current flow through amplifier E3; as is R9 for Q5. Capacitor C1 protects flip-flop E1/E2 from transient signals caused by external noise.

In our preferred embodiment, we use photodarlingtons as the photosensitive elements. Others, including the inventors of the light tester disclosed in U.S. Pat. No. 3,750,877, have used photomultipliers in can testers which have many disadvantages, including: they are bulky; exposure to high intensity light will damage them; they are made of glass and are, therefore, fragile; their sensitivity declines with use, with a maximum life in a can tester of six months to a year; they require high voltage power supply of 1500 to 1800 volts; and they are electrically noisy, i.e., extremely sensitive to voltage variations which can result in false rejects. Advantages of photodarlingtons over photomultipliers include the following: they are of small physical size on the order of a 1/5 of a thimble; overexposure to light is harmless; their sensitivity is stable throughout life; life is so long that it is infinite for practical purposes; and they require only about 2.5 volts power supply.

The preferred photodarlingtons are sold by Optron, Inc., under designation of OP 830 which are solid state and use a silicon diffused single chip monolithic structure. They are designed for use in low frequency on-off applications where extremely high sensitivities are required. The minimum light intensity detectable by this element is estimated to be about 0.005 milliwatts/cm$^2$. Since sensitivity or response to certain light of photodarlingtons is not uniform, they are selected to yield sensitivity between 4 and 8 on an arbitrary scale of 10, with 10 being too sensitive and 0 being not sensitive enough. This approach is based on the fact that sensitivity of photodarlingtons is proportional to dark current leakage, which can be measured. Furthermore, the photodarlingtons we employ have peak response in the infrared region which is beneficial for our purpose since infrared light is difficult to reflect from most surfaces. For this reason, we use high intensity quartz-iodine light source which have approximately 90% efficiency in terms of infrared output. The combination of such photodarlingtons and the high intensity quartz-iodine light source renders the photodarlingtons responsive substantially to direct light only. The following are optoelectric characteristic at 25° C of these photodarlingtons:

| light current | | dark current | collector emitter breakdown | saturation voltage | rise & fall time | angular response |
|---|---|---|---|---|---|---|
| min | max H | max | min | min TYP | TYP | degrees |
| mA | | nA | volts | volts | μ sec | Θ hp |
| 15 | — | 0.5 | 1000 | 15    5 | 1.2 | 20 | 10 |

Earlier, it was noted that total angular response for these photodarlingtons is 20°. This corresponds to the angular response of 10° given in above table since this figure respresents response from the center line, with the total response being double that amount.

A photodarlington is representative of a pair of phototransistors in a darlington configuration where emitter of one is connected to the base of the other and the collector of the other is connected to the collector of the first. The emitter of the second darlington is the negative terminal whereas the combined collectors form the positive terminal. In our application, we do not use the lead from the base.

In the array of photodarlingtons described in connection with our photosensitive device, a group of five of the darlingtons are connected to an operational amplifier. Each photodarlington is connected to a voltage source of 2.5 volts with collector at the positive potential. The emitter is connected to a negative potential through a load resistor of 200,000 ohms. Current flow from emitter to collector produces a voltage drop across the load resistor, amount of current being dependent on amount of light falling on the base of the photodarlington. Voltage drop across the load resistor provides input to operational amplifier where voltage difference is amplified about one million times, depending on circuit parameters. Output of operational amplifier provides a $T^2L$ transistor-transistor logic output of about 5 volts which is used to trigger a flip-flop, i.e., a multivibrator, which is connected as a latching circuit to illuminate light emitting diodes (LEDS), also referred to herein as flange light 210 and can body light 212. From the light emitting diodes, light is detected by a stationary photosensitive detector 220, output of which goes to electronic memory or a device of similar function for eventual ejection of a leaky can or retention of a good can.

FIG. 15 illustrates disposition of lighting fixtures, including upper fixture 228 and lower fixture 230. These fixtures are arcuate with an included angle of about 25°. Plurality of high intensity lamps 232 are arranged in the lighting fixtures with their axes parallel to axes of cans 8 which are moved between the upper and lower fixtures in a clamped disposition between a holder and a photosensitive device. Although not illustrated in FIG. 9 for the sake of not complicating the drawing, but shown generally in FIG. 2, the fixtures are rigidly disposed and remain stationary between rings 122, 124 with the upper fixture being secured above brace rods 126 and above the clamped cans whereas the lower fixture is disposed below the rotating cans between rings 122, 124. Such disposition of the fixtures is effected by securing the upper fixture by braces to rear plate 70 which allow this fixture to hang between rings 122, 124; the lower fixture is supported between rings 122, 124 by a stationary bracket 231 mounted on shaft 21. Bracket 231 also supports guide rail 30 between rings 122, 124. Lamps 232 are disposed lengthwise between rings 122, 124 and illuminate the can from all angles so that in case there is an opening in can body or can flange, a direct ray of light will be projected through the opening directly to the photosensitive device. In the preferred embodiment, we use 4 lamps in the upper fixture and 3 lamps in the lower fixture, each lamp being a high intensity quartz-iodine type with a rating of 500 watts. Such lamps have 90% efficiency in terms of infrared output compared to 30% for conventional tungsten bulbs.

The light tester described herein is driven by an eddy current motor of 230/460 volts, 3 phase, 60 cycles, which provides for variable speed. The motor is engaged by means of a chain to three drive sprockets mounted on shafts of respective wheels, as well as an idler sprocket which is used to obtain proper relative rotational direction of the wheels. It should be remembered that the feed wheel and discharge wheels rotate clockwise whereas the test wheel rotates counter clockwise, as viewed from the front of the light tester identified by front plate 72 in FIG. 9.

Since the tester can handle 1200 cans per minute and more, twelve can-producing lines of 100 cans per minute can be serviced by the tester. Should some of the can lines be inoperative for some reason, the speed of the motor is adjusted to permit the tester to handle the exact number of cans desired.

In FIG. 16, front plate 72 is shown with cam track 140 affixed to its interior surface. The cam track includes a plateau 238, ascending surface 236 and descending surface 240. When a can is transferred to the test wheel and clamped between a holder and a photosensitive device at a point just to the right of descending surface 240, roller 166 of the holder is off the cam track. The can is maintained in the clamped disposition as the test wheel rotates counter-clockwise for about 270° from about the 4:30 o'clock position through the test station until it reaches about the 8:30 o'clock position at a point just ahead of incline or descent surface 236 where transfer from the test wheel to the discharge wheel takes place. At about this point, i.e., 8:30 o'clock position, the roller on the holder engages incline surface 236 and as it travels upward onto plateau 238, the holder is withdrawn to an inoperable position allowing the can to be deposited into a cradle of the discharge wheel. The roller remains on the cam track for about 90°, or from about 7:30 to 4:30 on the clock, and then the cycle is repeated.

In operating the light tester described herein, the cans to be tested are conveyed to the feed wheel 22 via screw conveyor 32. As the cans in the feed wheel are conveyed past the stationary bumper roll A, which is at about the 1:30 o'clock position on the feed wheel shown in FIG. 2 and which is the same as bumper roll C shown in FIG. 8, bumper roll A displaces all the spools to the vacuum condition to retain all cans in the cradles. On their way to the feed wheel, each can is tested for the presence of a flange by cookie cutter detector 54 which signals electronic memory to reject a can, if its flange is missing or damaged. If a flange on a can is missing or damaged, the electronic memory activates a particular bumper roll B, see FIG. 8, to shift a particular spool to the right, see FIGS. 5, 6, and 7, to admit pressurized air to interior of the cradle through orifice 100 in order to expel the can into hopper 60. Bumper roll B is disposed at about the 5:30 o'clock position on the feed wheel.

If a can has a good flange in place, the memory device will not receive any signal and for this reason, bumper rolls B will remain inactive to allow the can to be retained in a cradle by means of vacuum until it is ready for transfer to the test wheel. It should be recalled that the vacuum condition of the cradles was effected by stationary bumper roll A which moves all spools to the vacuum condition. Can with a good flange is retained in the cradles by means of vacuum until stationary bumper roll C is reached, which is at about 9:00 o'clock position on the feed wheel. At this point, bumper roll C returns all spools to their neutral position where pressurized air and vacuum are cut off. As vacuum is gradually lost, the vacuum grip on each can is released and the can is guided by means of guide rail surface 30b, see FIG. 2, into transfer position from feed wheel 22 to test wheel 20. The transfer position is about the 10:30 o'clock position on the feed wheel, in which position, the horizontal axis of the can is brought into alignment with the axis passing through holder 136 and photosensitive device 138, see FIG. 9. When in this position, cam roller 166 comes off cam track 140 to clamp the can between holder 136 and photosensitive device 138. Once securely in place in the test wheel, the can is moved counterclockwise through the test station between light fixtures 228, 230 where it is illuminated from all possible angles. If there is an opening in the can flange, direct light will pass therethrough and be sensed by a photodarlington disposed in the outermost concentric circle which, in turn, will actuate flange light 210 on the back of photosensitive device 196. An opening in the can body will be detected by photodarlingtons in the inner concentric circles which will turn on can body light 212. With rotation of test wheel 20, can flange and can body lights 210, 212 will pass by photoreceiver 220. If any of these lights are on, they will be detected by sensor 222 or 224 and the signal will be conveyed to the electronic memory for processing.

Transfer from test wheel 20 to discharge wheel 24 is at a point on the discharge wheel of about 1:30 o'clock position. With the test wheel rotating counterclockwise and the discharge wheel rotating clockwise, roller 166 of holder 136 at this point ascends incline 236 of cam track 140, see FIG. 16, and disengages the holder from the can allowing the can to be guided by rail surface 30a into one of the cradles 27 on the discharge wheel. Rotation of the test wheel and the discharge wheel is such that the can is brought into proper disposition with respect to the cradle and this is effected through the single drive means and 1-1 gear interconnection between the three wheels. Should a can remain lodged in the test wheel between the holder and the photosensitive device, guide surface 30a of guide rail 30 also serves as a stripper rail to remove the can from the test wheel.

Once roller 166 of holder 136 reaches plateau 238 of cam track 140, it remains there for a dwell of about 90% during which, the holder is in an inoperative or disengaged position. Upon reaching descent surface 240, another can is brought into position and roller 166 actuates holder 136 to clamp the can between the holder and the photosensitive device 138 to commence another cycle.

After the can is placed into a cradle in the discharge wheel, bumper rolls D, shown at about the 1:30 o'clock position on the discharge wheel in FIG. 2, shifts a respective spool to vacuum, if the can is good, or a reject signal from the memory actuates bumper roll D to shift respective spool to pressurized air, if the can is a leaker. In either instance, the can continues around the discharge wheel, guided by rail surface 30a, until a point is reached at about the 3:00 o'clock position on the discharge wheel when guide rail surface 30a terminates with the can being ejected into hopper 62, if it is a leaker, or retained by vacuum until stationary bumper roll E shifts all spools to neutral and the can is extracted from the cradle by means of rail 34 onto rail 36 by conventional means and deposited at another station with the good cans. Bumper rolls D are a double acting rolls, such as rolls B shown in FIG. 8, whereas bumper roll E is a stationary roll, such as roll C shown in FIG. 8.

We claim:

1. Apparatus for automatically inspecting open-ended containers for presence of openings in their structure comprising a rotatable shaft; plurality of photosensitive devices mounted for rotation with the shaft; plurality of holders, corresponding in number to the number of the photosensitive devices, mounted for rotation with the shaft, with each holder disposed opposite a corresponding photosensitive device; each holder includes means for yieldably maintaining a container between a holder and a photosensitive device whereby the device shuts off the open end of the container from exterior light; means for feeding containers between cooperating holders and photosensitive devices; stationary test station, including a light source for illuminating exterior of containers passing therethrough with the photosensitive devices sensing light passing through any opening that may be present in the containers; and means for sorting good container from leakers in response to signals from the photosensitive devices.

2. Apparatus of claim 1 wherein each photosensitive device includes a plurality of photodarlingtons having light sensitivity to sense only direct light from the light source through an opening in a container and not reflected light from the interior thereof.

3. Apparatus of claim 2 wherein the containers have outwardly extending flanges, the apparatus including means for positioning the photodarlingtons in the photosensitive device so that a first group thereof senses any direct light from light source passing through the body of the containers and a second group of photodarlingtons which senses any direct light from the light source passing through the flange of the containers.

4. Apparatus of claim 3 wherein the photodarlingtons have a sensitivity in the range of 4 to 8 based on an arbitrary scale of 10, are functional within the total included angle of 20° and have peak response in the infrared region; whereas the light source includes a plurality of lamps of high infrared output arranged above and below the containers passing through the test station.

5. Apparatus of claim 4 wherein each photosensitive device includes a convex base with a plurality of openings in the base arranged in concentric circles, the openings being disposed at right angles to the base and retain the photodarlingtons, the outer circle of photodarlingtons being directed to receive light passing through any opening in the flange of the containers whereas remainder of photodarlingtons are directed to receive light passing through any opening in the body of the containers.

6. Apparatus of claim 5 including a can flange light and a can body light mounted on the photosensitive device, the flange light is connected to the photodarlingtons in the outer circle and lights up to provide visual readout whenever an opening is detected in a can flange whereas the can body light is connected to the remainder of the photodarlingtons and lights up to provide visual readout whenever an opening is detected in a can body.

7. Apparatus of claim 5 wherein each photosensitive device includes a circular sealing pad with an interior surface slanting outwardly for sealing interior of the container by being brought in contact with the flange of the container thus allowing testing of the flanges for openings therein by exposing the underside of the flange to light from the light source.

8. Apparatus of claim 7 including a reset device mounted before the test station for extinguishing any lighted flange and/or body lights at the beginning of each cycle.

9. Apparatus of claim 8 including an electronic memory and a photosensor device mounted beyond the test station for receiving signals from the flange and body lights and for signaling the electronic memory to actuate the sorting means.

10. Apparatus of claim 9 wherein the container is a drawn metal can body.

11. Apparatus for automatically inspecting open-ended containers with outwardly extending flange for presence of openings in their structure comprising a front and a rear plate both vertically disposed in spaced relationship; a feed shaft, test shaft and discharge shaft mounted perpendicularly between the front and rear plates, the test shaft being disposed between the other two shafts; a feed wheel rotatable clockwise mounted on the feed shaft provided with cradles for supporting containers, a test wheel rotatable counterclockwise mounted on the test shaft and a discharge wheel rotatable clockwise mounted on the discharge shaft provided with cradles for supporting containers; means for rotating the feed, test and discharge wheels in unison; means for conveying containers to the feed wheel; means for transferring containers from feed wheel to test wheel; means for transferring containers from test wheel to discharge wheel; a plurality of holders with yieldable means mounted on the test wheel and being rotatable therewith; a plurality of photosensitive devices, corresponding in number to the number of holders, disposed in spaced opposed relationship to the holders on the test wheel which block the open end of containers and cooperate with the holders to clamp a container between each pair of opposed holders and devices, with any light entering interior of a container being detected by the photosensitive device; stationary test station, including a light source provided in association with the test wheel for illuminating exterior of the containers; and means for sorting good cans from leakers in response to the photosensitive devices.

12. Apparatus of claim 11 wherein the conveying means includes a pair of side by side screws with screw flights of an extent to allow nestling of containers therein; means for driving the screws in unison in timed relationship to the rotation of the feed wheel; a plate disposed in parallel spaced relationship to the screws holding the containers spaced between the screw flights; proximity switch mounted at the downstream end of the conveying means for sensing presence of containers; flange detector, actuatable by the proximity switch, for detecting presence of flanges on the containers; and means responsive to signals from the flange detector, mounted on the feed wheel, for ejecting containers without flanges or containers with damaged flanges at a predetermined station.

13. Apparatus of claim 11 including spool valves disposed through bores in the feed and discharge wheels, one spool valve associated with each cradle; each of the spool valves having a pressure port and a vacuum port; a pair of separate compartments in each of the feed and discharge shafts, one compartment being under pressure the other under vacuum; a pressure aperture leading through each feed and discharge shaft and each feed and discharge wheel to connect the pressure compartment with the bore in which the spool valve is disposed and a vacuum aperture leading through each feed and discharge shaft and each feed and discharge wheel to connect the vacuum compartment with the same bore; a cradle aperture leading from the bore through each feed and discharge wheel into and through each cradle; means for shifting each spool valve to bring either the pressure or vacuum compartment in communication with the cradle aperture through the shafts, wheels and either pressure or vacuum ports to either expel from or retain containers in the cradles by means of pressurized air or vacuum.

14. Apparatus of claim 13 including an auxiliary port on each spool valve disposed between the pressure and vacuum ports; a spool compartment in each spool valve sealed from outside and the three ports; spool aperture providing communication between the spool compartment and the auxiliary port, each spool valve in its neutral position being disposed in a bore with its auxiliary port shut except for communication with the cradle aperture and relative disposition of the ports and spool apertures is such that when the cradle aperture is under vacuum, the auxiliary port is connected to the pressure compartment through the pressure port and the spool aperture allowing pressurized air to seep into the spool compartment which then seeps into the cradle aperture when the spool valve is returned to its neutral position to allow quicker release of a container from the cradle.

15. Apparatus of claim 13 wherein each photosensitive device includes a plurality of photodarlingtons having light sensitivity to sense only direct light from the light source through an opening in the container and not reflected light from the interior thereof.

16. Apparatus of claim 15 further including means for positioning the photodarlingtons in the photosensitive device so that a first group thereof senses any direct light from light source passing through the body of the containers and a second group of photodarlingtons for sensing any direct light from the light source passing through the flange of the containers.

17. Apparatus of claim 16 wherein the photodarlingtons have a sensitivity in the range of 4 to 8 based on an arbitrary scale of 10, are functional within the total included angle of 20° and have peak response in the infrared region; whereas the light source includes a plurality of lamps of high infrared output arranged above and below the containers passing through the test station.

18. Apparatus of claim 17 wherein each photosensitive device includes a convex base with a plurality of openings in the base arranged in concentric circles, the openings being disposed at right angles to the base and retain the photodarlingtons, the outer circle of photodarlingtons being directed to receive light through the flange of the containers whereas remainder of photodarlingtons are directed to receive light through the body of the containers.

19. Apparatus of claim 18 including a can flange light and a can body light mounted on the photosensitive device, the flange light is connected to the photodarlingtons in the outer circle and lights up to provide visual readout whenever an opening is detected in a can flange whereas the can body light is connected to the remainder of the photodarlingtons and lights up to provide visual readout whenever an opening is detected in a can body.

20. Apparatus of claim 19 wherein each photosensitive device includes a circular sealing pad with an interior surface slanting outwardly for sealing interior of the container by being brought in contact with the flange of the container thus allowing testing of the flanges for openings therein by exposing the underside of the flange to light from the light source.

21. Apparatus of claim 13 including a proximity switch in association with the conveying means for sensing presence of containers; means for detecting presence or absence of flanges on containers which is actuated by the proximity switch; a first bumper on the feed wheel disposed just ahead of the point of container transfer from the conveying means to the feed wheel for shifting all spool valves to the vacuum position in order to retain containers in their cradles; a second bumper disposed between the first and third bumpers for shifting certain of the spool valves to an air pressure position, in response to a signal from memory device, to eject cans without flanges or cans with damaged flanges; and a third bumper on the feed wheel for shifting the spool valves to the neutral position disposed at a point prior to container transfer from the feed wheel to the test wheel.

22. Apparatus of claim 21 including a first bumper on the discharge wheel disposed just ahead of container transfer from the test wheel to the discharge wheel for shifting the spool valves to either pressure or vacuum side to either expel a container from a cradle at an appropriate point or to retain a container in the cradle; discharge rail associated with the discharge wheel disposed ahead of the first bumper for extracting containers from the discharge wheel; and second bumper on the discharge wheel disposed between the first bumper and the discharge rail for shifting the spool valves to a neutral position.

23. Apparatus for testing open-ended containers for openings therein comprising a rotatable feed carrier, a rotatable test carrier and a rotatable discharge carrier, the containers being moved from the feed to the test and finally to the discharge carrier; a plurality of holders mounted on the test carrier, each holder including yieldable means for clamping a container; a plurality of photosensitive devices, corresponding in number to the number of the holders disposed on the test carrier in spaced, opposed relationship to the holder; a stationery test station, including a light source for illuminating exterior of the containers, the containers being adapted to be clamped between pairs of holders and photosensitive devices and advanced through the test station where light passing through an opening in a container would be detected by the photosensitive devices; and means for sorting good containers from leakers in response to the photosensitive devices.

24. Apparatus of claim 23 wherein the holder includes a block; a bore through the block; a holder stem passing through the bore having exposed rear and front ends; a linkage secured at one end to the rear end of the holder stem for shifting the holder stem between operative and inoperative positions, the operative position being one where the holder is in the forward position with a container clamped between a holder and a photosensitive device whereas the inoperative position is one where the holder is withdrawn from the clamping position.

25. Apparatus of claim 24 wherein the holder includes a roller affixed to the other end of the linkage and a pivot pin securing the linkage at a point between its ends to the block causing the linkage to pivot about the pivot pin when advancing or retracting the holder stem.

26. Apparatus of claim 25 including a front and rear plates disposed in spaced, vertical relationship; three shafts extending between the plates in horizontally spaced disposition with the test carrier mounted on the middle shaft and the other two carriers mounted on the outer shafts; an arcuate cam track affixed to the interior face of the front plate in position to be engaged by the holder roller for shifting the holder stem to inoperable position when the roller engages the cam track, the holder stem being in operable position when the roller is disengaged from the cam track.

27. Apparatus of claim 26 including an elastic pad affixed to the front end of the holder stem; arcuate extent of the cam track is about 90°; and the yieldable means on the holder is a spring for biasing the pad against the bottom of a can when the holder is in operable position.

28. Apparatus of claim 26 including a dead-end bore in the holder stem extending from the front end of the stem inwardly; a port through the stem communicating with the bore; a transverse bore in the holder block which is in communication with the stem port when the holder is in operable position; a valve with a passage therethrough disposed in the transverse bore, the passage being in alignment and communicating with the stem port when the holder is in operable position, with the port being open to the atmosphere when the holder is in inoperable or retracted position; means for delivering vacuum to the valve for facilitating retention of a container against the holder when the holder is in its inoperable disposition.

29. Apparatus for testing open-ended containers for openings therein comprising a rotatable feed wheel, a rotatable test wheel and a rotatable discharge wheel, the wheels being mounted on respective shafts and the containers being moved from the feed to the test and finally to the discharge wheel; cradles mounted on feed and discharge wheels; a plurality of holders mounted on the test wheel; a plurality of photosensitive devices, corresponding in number to the number of the holders, disposed on the test wheel in spaced, opposed relationship to the holders; a stationery test station, including a light source for illuminating exterior of the containers, the containers being adapted to be clamped between pairs of holders and photosensitive devices and advanced through the test station where light passing through any opening in containers would be detected by the photosensitive devices; means for sorting good containers from leakers in response to the photosensitive devices; spool valves disposed through bores in the feed and discharge wheels, one spool valve associated with each cradle; each of the spool valves having a pressure port and a vacuum port; a pair of separate compartments in each of the feed and discharge shafts, one compartment being under pressure the other under vacuum; a pressure aperture leading through each feed and discharge shaft and each feed and discharge wheel to connect the pressure compartment with the bore in which the spool valve is disposed and a vacuum aperture leading through each feed and discharge shaft and each feed and discharge wheel to connect the vacuum compartment with the same bore; a cradle aperture leading from the bore through each feed and discharge wheel into and through each cradle; means for shifting each spool valve to bring either the pressure or vacuum compartment in communication with the cradle aperture through the shafts, wheels and either pressure or vacuum ports to either expel from or retain containers in the cradles by means of pressurized air or vacuum.

30. Apparatus of claim 29 including an auxiliary port on each spool valve disposed between the pressure and vacuum ports; a spool compartment in each spool valve sealed from outside and the three ports; spool aperture providing communication between the spool compartment and the auxiliary port, each spool valve in its neutral position being disposed in a bore with its auxiliary port shut except for communication with the cradle aperture and relative disposition of the ports and spool apertures is such that when the cradle aperture is under vacuum, the auxiliary port is connected to the pressure compartment through the pressure port and the spool aperture allowing pressurized air to seep into the spool compartment which then seeps into the cradle aperture when the spool valve is returned to its neutral position to allow quicker release of a container from the cradle.

31. Apparatus for testing open-ended containers for openings therein comprising a rotatable feed carrier, a rotatable test carrier and a rotatable discharge carrier, the containers being moved from the feed to the test and finally to the discharge carrier; a plurality of holders mounted on the test carrier; a plurality of photosensitive devices corresponding in number to the number of the holders disposed on the test carrier in spaced, opposed relationship to the holders; a stationery test station, including a light source for illuminating exterior of the containers, the containers being adapted to be clamped between pairs of holders and photosensitive devices and advanced through the test station where light passing through an opening in a container would be detected by the photosensitive devices; means for sorting good containers from leakers in response to the photosensitive devices; the photosensitive devices have optimum response in the infrared region and the light source has a high output of infrared light whereby reflectance of such light from interior of containers is minimized.

32. Apparatus of claim 31 wherein the light source is a plurality of high intensity quartz-iodine lamps and the photosensitive device includes a plurality of photodarlingtons.

33. Apparatus of claim 32 wherein the photodarlingtons are of the type known as Optron's OP 830 and the containers are drawn metal cans.

34. Method of testing open-ended containers for presence of openings therein comprising clamping containers between pairs of holders and photosentitive devices mounted on a test carrier with the photosensitive devices blocking the open ends of the containers; illuminating exterior of the containers at a test station; detecting light passing through any opening in containers by means of the photosensitive devices; and sorting good containers from leakers.

35. Method of claim 34 including the step of reducing reflectance of light from interior surfaces of the containers by using high intensity quartz-iodine lamps of high infrared light output and sensing such light with a plurality of photodarlingtons disposed in the photosensitive device which have optimum response in the infrared region.

36. Method of claim 34 including the steps of providing a feed carrier on one side of the test carrier and a discharge carrier on the other side; transferring containers from the feed carrier to the test carrier by guiding them against a guide rail on the test carrier to a position between a holder and a photosensitive device; transferring containers from test carrier to discharge carrier by guiding them against a guide rail on the test carrier into individual cradles on the discharge carrier.

37. Method of claim 36 including the step of applying vacuum to the underside of the containers through the holders to facilitate retention thereof in the test wheel from the time the containers are clamped in position and until they are unclamped.

38. Method of claim 36 including the steps of applying either pressurized air or vacuum to the cradles affixed to the feed carrier and discharge carrier for either ejecting or retaining containers in the cradles.

39. Method of claim 38 including the step of breaking the vacuum on cradles by means of a pulse of pressurized air.

40. Method of claim 36 including the steps of sensing light passing through an opening in a container by a plurality of photodarlingtons disposed in the photosensitive device; directing a first set of the photodarlingtons towards the flange of containers; directing a second set of the photodarlingtons at the body of the containers; energizing a flange light for visual inspection in response to signals from the first set of photodarlingtons; and energizing a body light for visual inspection in response to signals from the second set of photodarlingtons.

* * * * *